US010610300B2

(12) United States Patent
Koch et al.

(10) Patent No.: US 10,610,300 B2
(45) Date of Patent: Apr. 7, 2020

(54) METHOD FOR EVALUATING TREATMENT-RELEVANT SPATIAL INFORMATION

(71) Applicants: Martin Willibald Koch, Nürnberg (DE); Norbert Strobel, Heroldsbach (DE)

(72) Inventors: Martin Willibald Koch, Nürnberg (DE); Norbert Strobel, Heroldsbach (DE)

(73) Assignee: Siemens Aktiengesellschaft, München (DE)

( * ) Notice: Subject to any disclaimer, the term of this patent is extended or adjusted under 35 U.S.C. 154(b) by 1169 days.

(21) Appl. No.: 14/771,754

(22) PCT Filed: Jul. 5, 2013

(86) PCT No.: PCT/EP2013/064269
§ 371 (c)(1),
(2) Date: Aug. 31, 2015

(87) PCT Pub. No.: WO2014/131467
PCT Pub. Date: Sep. 4, 2014

(65) Prior Publication Data
US 2016/0199135 A1 Jul. 14, 2016

(30) Foreign Application Priority Data
Mar. 1, 2013 (EP) .................... 13157407

(51) Int. Cl.
*A61B 34/10* (2016.01)
*G06T 7/00* (2017.01)
(Continued)

(52) U.S. Cl.
CPC .......... *A61B 34/10* (2016.02); *A61B 5/02028* (2013.01); *G06T 7/0016* (2013.01);
(Continued)

(58) Field of Classification Search
CPC ................ A61B 34/10; A61B 5/02028; A61B 2034/105; A61B 2034/107; G06T 7/30;
(Continued)

(56) References Cited

U.S. PATENT DOCUMENTS

2005/0065421 A1* 3/2005 Burckhardt ............ A61B 6/032
600/407
2011/0295515 A1* 12/2011 Grady .................. A61B 5/4064
702/19

(Continued)

FOREIGN PATENT DOCUMENTS

WO WO2011009121 A1 1/2011

OTHER PUBLICATIONS

Brost A. et al.: "AFiT—Atrial Fibrillation Ablation Planning Tool," in: Vision, Modeling, and Visualization (2011) VMV'11, pp. 223-230, 2011.

(Continued)

*Primary Examiner* — Peter Luong
(74) *Attorney, Agent, or Firm* — Lempia Summerfield Katz LLC

(57) ABSTRACT

The invention relates to a method for evaluating treatment-relevant spatial anatomical information among different data sets of the heart, the method comprising the steps of: —determining a reference anatomical 3 dimensional data set of the heart, —providing a first anatomical 3 dimensional data set of the heart, the first anatomical 3 dimensional data set comprising first treatment-relevant spatial anatomical information, —providing a second anatomical 3 dimensional data set of the heart, the second anatomical 3 dimensional data set comprising second treatment-relevant spatial anatomical information, —registering the reference data set to the first and the second data sets, —transferring the treatment relevant spatial anatomical information of the first (Continued)

and the second data set to the reference data set in order to generate a first transferred treatment-relevant spatial anatomical information on the reference data set and a second transferred treatment-relevant spatial anatomical information on the reference data set —evaluating the first and the second transferred treatment-relevant spatial anatomical information.

15 Claims, 7 Drawing Sheets

(51) Int. Cl.
    *A61B 5/02*           (2006.01)
    *G06T 7/30*           (2017.01)

(52) U.S. Cl.
    CPC .......... *G06T 7/30* (2017.01); *A61B 2034/105* (2016.02); *A61B 2034/107* (2016.02); *G06T 2200/04* (2013.01); *G06T 2207/20112* (2013.01); *G06T 2207/20128* (2013.01); *G06T 2207/20212* (2013.01); *G06T 2207/30048* (2013.01)

(58) Field of Classification Search
    CPC ............... G06T 7/0016; G06T 2200/04; G06T 2207/20112; G06T 2207/20128; G06T 2207/20212; G06T 2207/30048
    See application file for complete search history.

(56) References Cited

U.S. PATENT DOCUMENTS

| | | | | |
|---|---|---|---|---|
| 2012/0232853 | A1* | 9/2012 | Voigt | G06F 19/321 703/1 |
| 2015/0023777 | A1* | 1/2015 | Rawcliffe | F04D 27/0207 415/1 |

OTHER PUBLICATIONS

Hastentefel M. et al.: "A Novel Method for Planning and Visualization of Ablation Lines for Atrial Fibrillation Treatment," in: Computing in Cardiology Conference, Sep. 19-22, 2004, Chicago, Illinois, USA, pp. 13-16, 2004.

Isgum I et al.: "Multi-Atlas-Based Segmentation With Local Decision FusionáApplication to Cardiac and Aortic Segmentation in CT Scans," IEEE Transactions on Medical Imaging, IEEE Service Center, Piscataway, vol. 28, No. 7, pp. 1000-1010, XP011249667, ISSN: 0278-0062, DOI: 10.1109fTMI.2008.2011480, 2009.

Keustermans, Johannes et al: "Automated planning of ablation targets in atrial fibrillation treatment," in: Medical Imaging 2011: Image Processing, SPIE, 1000 20th St. Bellingham, vol. 7962, No. 1, pp. 1-7 XP060009376, DOI:10.1117/12.878250, 2011.

Kirisli Hortense et al: "Fully automatic cardiac segmentation from 3D CTA data: a multi-atlas based approach," Proceedings of SPIE, vol. 7623, pp. 762305-762305-9, XP55085418, ISSN: 0277-786X, DOI: 10.1117/12.838370, 2010.

PCT International Search Report and Written Opinion of the International Searching Authority dated Nov. 7, 2013 for corresponding PCT/EP2013/064269.

Rikxoort Eva M. et al: "Adaptive local multi-atlas segmentation: Application to the heart and the caudate nucleus," in: Medical Image Analysis, vol. 14, No. 1, pp. 39-49, XP55084891, ISSN: 1361-8415,DOI: 10.1016/j.media.2009.10.001, 2010.

Arentz, Thomas et al: "Small or large isolation areas around the pulmonary veins for the treatment of atrial Fibrillation?" in: Circulation, vol. 115, No. 24, pp. 3057-3063. 2017

Bourier, Felix, et al. "Pulmonary vein isolation supported by MRI-derived 3D-augmented biplane fluoroscopy: a feasibility study and a quantitative analysis of the accuracy of the technique." Journal of Cardiovascular Electrophysiology 24.2 (2013): 113-120.

De Buck, Stijn, et al. "An augmented reality system for patient-specific guidance of cardiac catheter ablation procedures." IEEE Transactions on Medical Imaging 24.11 (2005): 1512-1524.

Heimann, Tobias, and Flans-Peter Meinzer. "Statistical shape models for 3D medical image segmentation: a review." Medical image analysis 13.4 (2009): 543-563.

Jolliffe I.; "Principal Component Analysis", John Wiley & Sons, Encyclopedia of Statistics in Behavioral Science; vol. 3; pp. 1580-1584; online http://www.mrw.interscience.wiley.com/emrw/ 9780470013199/esbs/article/bsa501/current/pdfISBN: 978-0-470-86080-9; XP002487258; 2005.

Kautzner, Josef, et al. "Anatomy of the Left Atrium and Pulmonary Veins-Lessons Learned from Novel Imaging Techniques." Journal-Anatomy of the Left Atrium and Pulmonary Veins-Lessons Learned from Novel Imaging Techniques (2006). pp. 89-90.

Koch, Martin, et al. "Navigation system with contact force assessment to guide pulmonary vein isolation procedures." 23rd Conference of the Society for Medical Innovation and Technology (SMIT),(Tel Aviv, Israel). 2011. pp. 1-2.

Myronenko, Andriy, and Xubo Song. "Point set registration: Coherent point drift." IEEE transactions on pattern analysis and machine intelligence 32.12 (2010): 2262-2275.

Myronenko, Andriy, et al. "Non-rigid point set registration: Coherent point drift." Advances in neural information processing systems. 2007. pp. 1009-1016.

Tung, Roderick et al: "Catheter Ablation of Atrial Fibrillation" in: Circulation vol. 126, No. 2, pp. 223-229, 2012.

\* cited by examiner

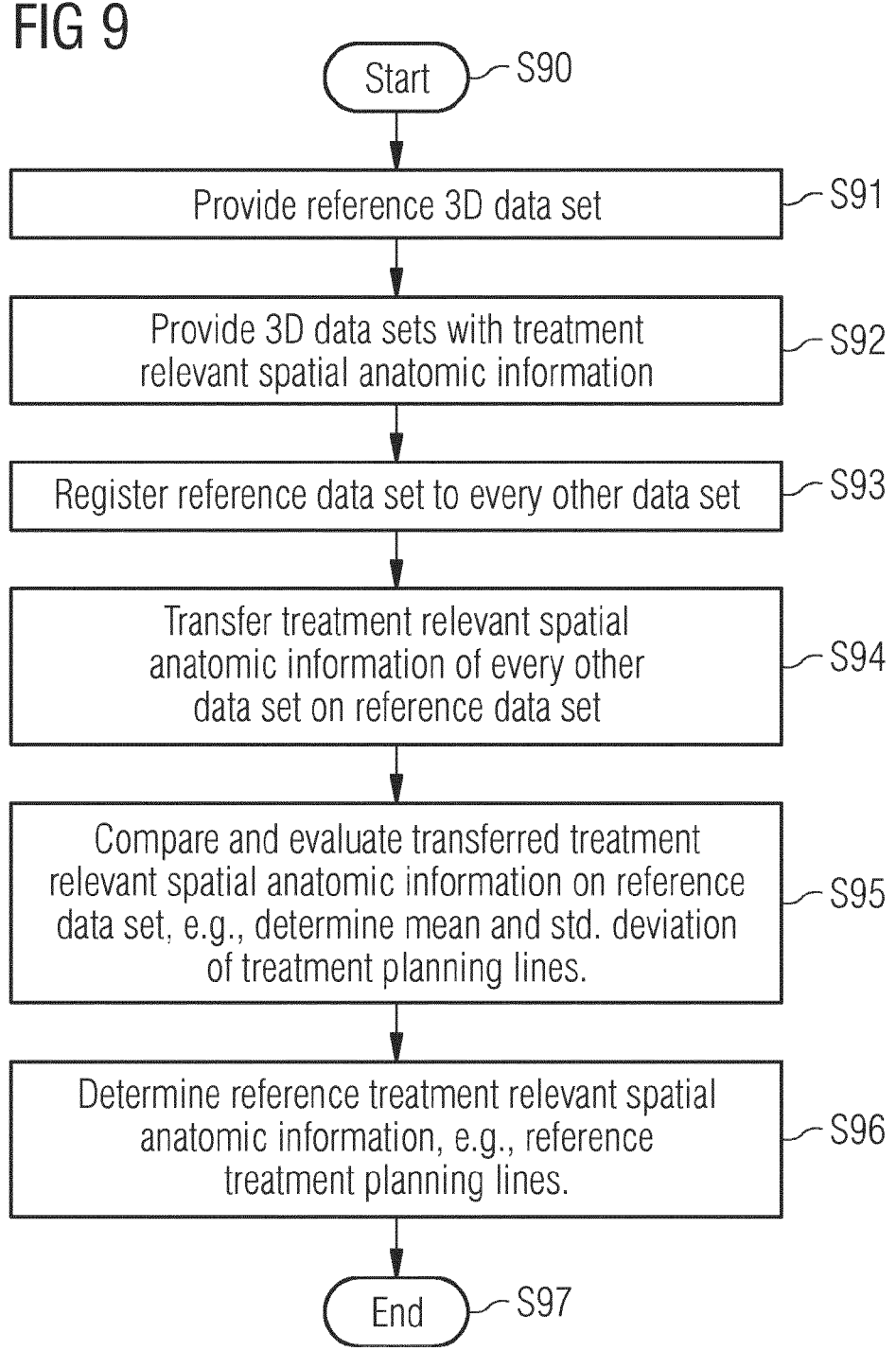

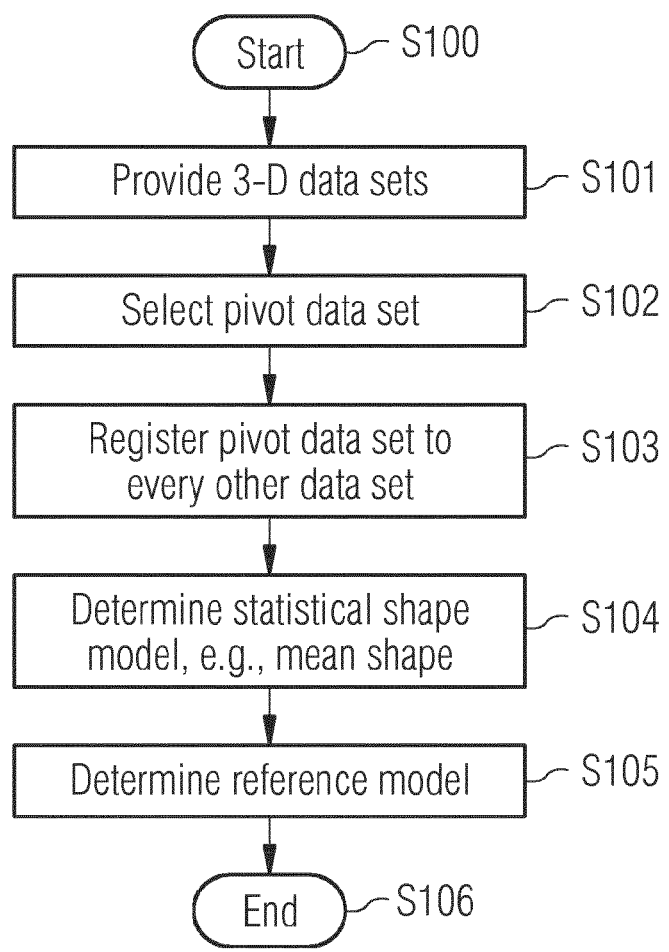

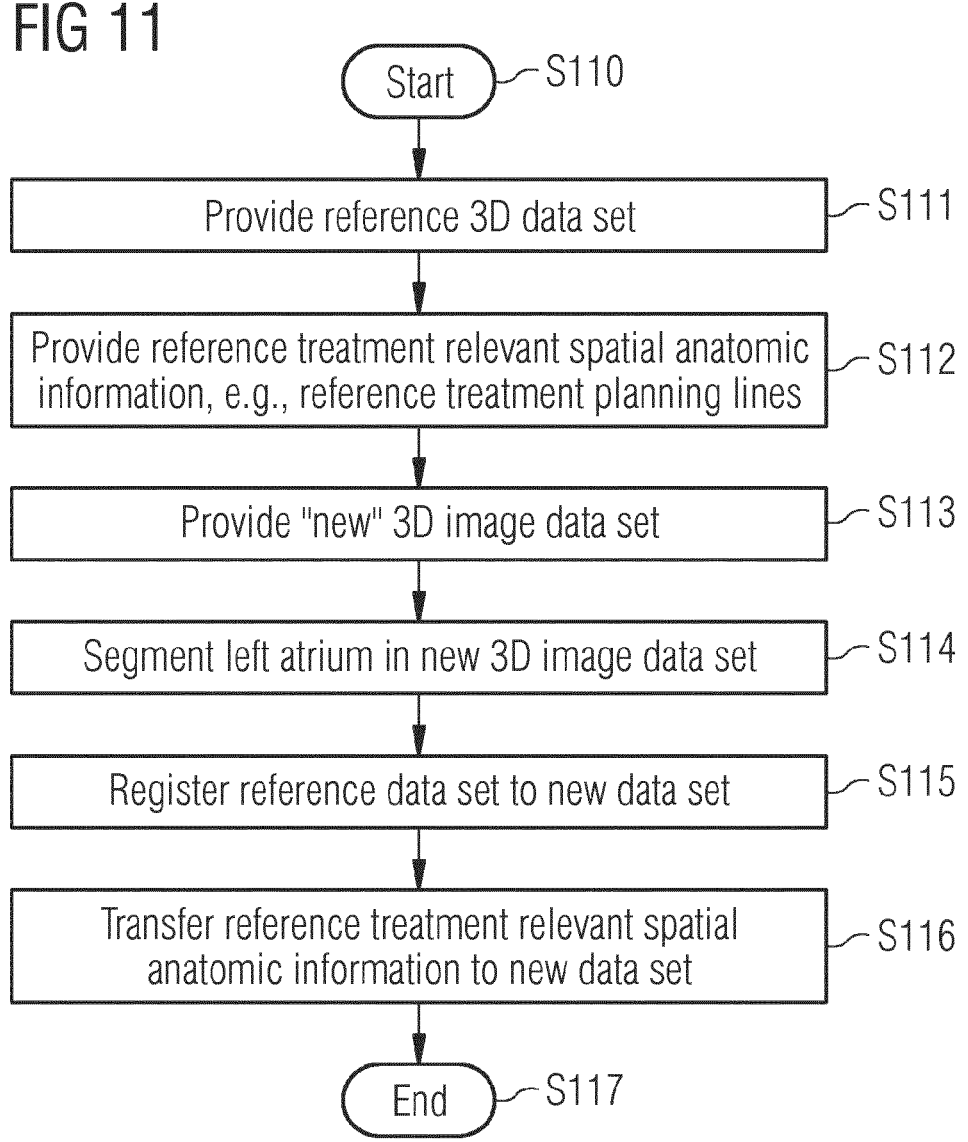

METHOD FOR EVALUATING TREATMENT-RELEVANT SPATIAL INFORMATION

The invention relates to a method for evaluating treatment-relevant spatial anatomical information among different data sets of the heart and to a system therefor Statistical shape models are widely used today in different fields of medical image processing. A common application is the use as prior information for segmentation of 3-D medical image data [1]. The left atrium is a challenging structure, as it shows a large amount of variation in surface topology and shape across different patients. In addition to the anatomical differences among subjects, there is the aspect of cardiac motion which leads to deformations of the left atrium in different heart phases. In electrophysiology ablation procedures, a model of the underlying anatomical structure could be used for planning of the intervention as, e.g., suggested by Keustermans et al. using patient-specific 3-D data sets for planning of atrial fibrillation treatment [2].

Since electrophysiology (EP) procedures involve fluoroscopic guidance, C-arm X-ray devices with image overlay functionality, fusing soft-tissue information with live fluoro images, offer an alternative navigation approach to mapping systems [3, 4]. For EP procedures, these systems can be used to merge soft-tissue heart information derived from pre-procedurally acquired 3-D data sets as well as planning information with live fluoroscopy during the intervention [5]. A first approach for planning of atrial fibrillation has been presented by Hastenteufel et al. [6]. More recently, Brost et al. [7] proposed a system for interactive planning of EP procedures, especially atrial fibrillation ablation procedures involving cryo-balloons. An example of pre-planned ablation lines for PVI is shown in FIG. 1. Ablation lines are one example for treatment-relevant spatial anatomical information. The use of pre-planned ablation lines is not restricted to fluoro overlay navigation. This kind of annotation can also be helpful when performing PVI using a mapping system, e.g. CARTO 3 (Biosense Webster, Diamong Bar, Calif., USA) or Ensite Velocity (St. Jude Medical, St. Paul, Minn., USA).

Pulmonary vein isolation is the treatment of choice for paroxysmal atrial fibrillation with a reported success rate of over 70% [8]. PVI is also applied to persistent AFib, however with lower success rate of just over 50%. The structure of the left atrium is very complex. There are critical areas within the left atrium, e.g. the left atrial appendage or the area close to the esophagus, that should be avoided or treated with special care during ablation procedures. There are different strategies to perform PVI. Two common strategies are segmental ablation and ipsilateral pulmonary vein (PV) isolation. Arentz et al. investigated the influence of the isolation area around the PVI on the procedure outcome. Based on their findings, the ipsilateral ablation strategy is advantageous [9].

Personalized planning of ablation lines for electrophysiology procedures offers the potential to improve procedure success while lowering the risk to the patient. As of today, there has, however, not been an investigation on how ipsilateral ablation lines differ across similar cases.

Thus, the need exists to further improve the evaluation of treatment-relevant spatial anatomical information of ablation lines. This need is met by the features of the independent claims. Further embodiments are described in the dependent claims.

According to a first aspect, a method for evaluating treatment-relevant spatial anatomical information among different data sets of the heart is provided. In one step, a reference anatomical three-dimensional data set of the heart is determined. Furthermore, a first anatomical three-dimensional data set of the heart is provided, which comprises first treatment-relevant spatial anatomical information. A second anatomical three-dimensional data set of the heart with second treatment-relevant spatial anatomical information is provided. The reference data set is registered to the first and the second data set. In a further step, the treatment-relevant spatial anatomical information of the first and of the second data sets are transferred to the reference data set in order to generate a first transferred treatment-relevant spatial anatomical information on the reference data set and a second transferred treatment-relevant spatial anatomical information on the reference data set. Additionally, the first and the second transferred treatment-relevant spatial anatomical information is evaluated.

As the treatment-relevant spatial anatomical information ablation planning lines of the left atrium may be used.

The step of evaluating the first and the second transferred treatment-relevant spatial anatomical information can comprise the step of determining at least one of a mean value or standard deviation of the first and the second transferred treatment-relevant spatial anatomical information on the reference data set. Furthermore, the step of evaluating the transferred treatment-relevant spatial anatomical information may contain the step of indicating both pieces of information on the reference data set, e.g. the indication of both transferred ablation lines on the reference data set.

According to a further aspect, a plurality of further anatomical three-dimensional data sets of the heart may be provided with corresponding treatment-relevant spatial anatomical information. The reference anatomical three-dimensional data set can be registered to each of the further data sets and the treatment-relevant spatial anatomical information of each of the further data sets is transferred to the reference data set in order to determine transferred treatment-relevant spatial anatomical information on the reference data set for each of the further data sets.

The part of the heart that is of special interest in the present invention can be the left atrium of the heart.

Furthermore, it is possible to determine an average anatomical three-dimensional data set of the atrium based on at least the first and second data sets and an average treatment-relevant spatial anatomical information can be determined on the reference data set taking into account at least the first and the second transferred treatment-relevant spatial anatomical information.

Preferably the reference anatomical three-dimensional data set, the first and second data set and the further anatomical three-dimensional data sets of the atrium are each provided as a mesh structure, and a non-rigid mesh registration is used to register one data set to the other data sets. One possible registration method is the coherent point drift method. However, any other registration method may be used.

The invention may also be used for planning an interventional treatment. A new three-dimensional data set of the atrium is provided and registered to the reference data set in order to determine treatment-relevant spatial anatomical information for the new data set based on the transferred treatment-relevant spatial anatomical information of the reference data set.

Furthermore, it is possible that different reference data sets of the atrium are generated in order to take into account different heart anatomies, and for each of the different reference data sets transferred treatment-relevant spatial anatomical information is evaluated.

BRIEF DESCRIPTION OF THE DRAWINGS

The invention will be described in further detail with reference to the accompanying drawings. In the figures, FIG. 9 shows a schematic flow chart including exemplary steps to evaluate treatment areas of several data sets on a reference data set, FIG. 10 shows a flow chart comprising steps that are carried out to compute a reference data set, and FIG. 11 shows a flow chart comprising steps of applying reference treatment-relevant spatial anatomical information to a new data set.

DETAILED DESCRIPTION

Figure 1:
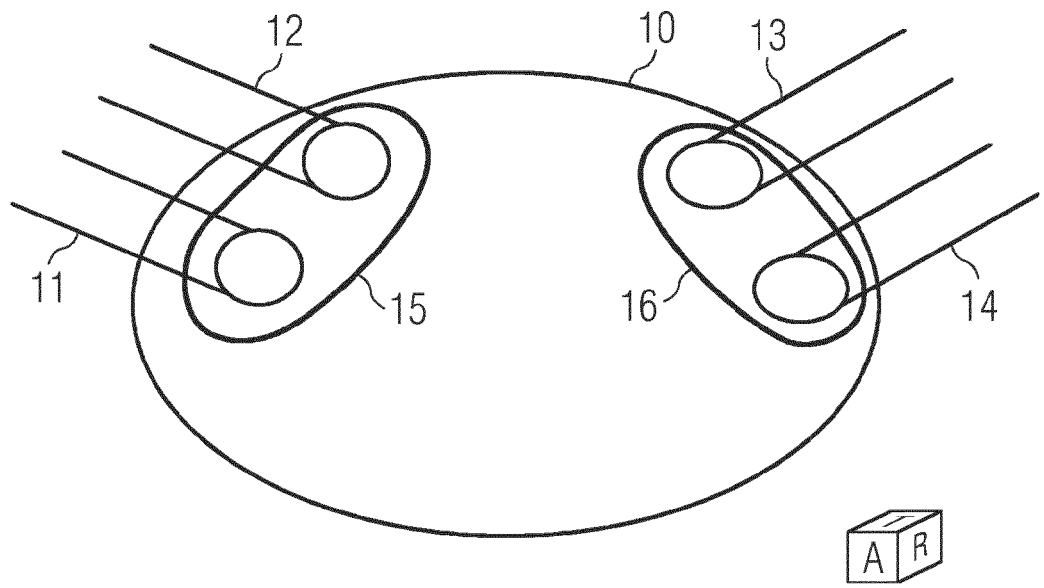
FIG. 1 shows a schematic view of a left atrium with planned ipsilateral ablation lines.

We present a novel method to investigate this problem by comparing pre-planned ablation lines defined by an experienced clinician. Although actual ablation lines may differ from their targets, a comparison among desirable ablation lines does provide insight into how much ablation lines may vary along certain parts of the left atrium.

We propose a framework for transfer of ablation planning information among different left atria heart models. Initially, a statistical shape model of the left atrium is generated to serve as a common basis. This approach is possible to transfer (spatially organized) annotations from input data to the previously computed common model. By projecting the different annotations onto to the common model, we can compare the different annotations and extract common features. By way of example, this makes it possible to compare different planning structures used in the context for atrial fibrillation ablation. Further on, it can be used as basis for an automatic planning approach. When applied to planning an atrial fibrillation ablation, different anatomical configurations of the left atrium have to be considered. This could be addressed by using a common basis for each configuration, e.g. for pulmonary veins, a common pulmonary vein or supernumerary vein.

The left atria are segmented from 3-D data sets (CT, C-arm CT, MRI) and modeled as triangle meshes. The correspondence between different left-atrial models is calculated via non-rigid registration of the model. Transfer of planning lines from the mesh-model A to mesh-model B is carried out as follows: First, model A is registered to model B. Afterwards, the planning data from model A is projected to model B.

The proposed solution can contain the following contributions: First of all, it uses a non-rigid point cloud based registration algorithm, for example coherent point drift, to generate a statistical shape model of the left atrium.

Secondly, spatially organized information, e.g. pulmonary vein isolation ablation planning lines are transferred and merged across multiple specific anatomies.

The statistical shape model of the left atrium can be used as a reference model to perform RF ablation planning, e.g. for pulmonary vein isolation (PVI). The second aspect enables us to transfer these annotations onto new unseen mesh models. This functionality can be used for automatic procedure planning.

This invention proposes a method for left atrium shape modeling using non-rigid point cloud registration. In our approach, we generate the shape model from 3-D magnetic resonance imaging (MRI) volume data sets. We exclusively used data sets of left atria with four pulmonary veins, which reflects the most common anatomic configuration [10]. First, the relevant structure was segmented and represented as triangle mesh. Then we used the Coherent Point Drift (CPD) algorithm [11] to pairwise align meshes via non-rigid point cloud registration. Basically, CPD registration is performed based on a Gaussian Mixture Model (GMM) framework and a regularization of the displacement field. Benefits of the CPD algorithm are the generation of smooth deformation fields while being robust against noise and outliers [11].

Left atrium mesh models of ten subjects were extracted from contrast enhanced 3-D MRI volume data sets. The MRI data sets were acquired with a resolution of 256×256×68 voxels. The in-plane pixel spacing was 1.23×1.23 mm and the slice thickness 1.5 mm. The left atrium was segmented from MRI voxel data sets using a semi-automatic segmentation software (syngo InSpace EP, Siemens AG, Forchheim, Germany). The segmentation process is initialized by manually selecting a point inside the left atrium. Based on this seedpoint, the complete left atrium is segmented automatically. The segmentation results are represented as triangle meshes.

For registration, let us consider the mesh as a point cloud M consisting of N points $x_i \in R^3$ $$M = m = [x_1^T, \ldots, x_N^T]^T \in R^{3N} \quad (1)$$

In a first step, we selected one left atrium mesh model as a reference mesh. The reference mesh was chosen based on visual inspection to clearly express the LA anatomy. The reference mesh $m_{Ref}$ is then registered to a set of sample meshes $\{m_t\}_{t=1}^T$, with T=9, using the CPD algorithm. All meshes have the same anatomical orientation, and are zero centered before applying the registration.

We used the coherent point drift (CPD) algorithm to register the reference mesh to the set of sample meshes. CPD follows a probabilistic approach by considering the alignment of the two point sets as a probability density estimation problem. The basic idea is to fit the GMM centroids, represented by the points of the reference mesh $m_{Ref}$, to the sample mesh $m_t$, by maximizing the likelihood. This optimization is performed with the expectation maximization algorithm. During the optimization process, the GMM centroids are forced to move coherently as a group, to ensure preservation of the topological structure of the point set. The displacement function v for the reference mesh is defined as $$\hat{m}_{Ref} = m_{Ref} + v(m_{Ref}) \quad (2)$$

with $m_{Ref}$ as the initial centroid positions, $\hat{m}_{Ref}$ and v, respectively are obtained by minimizing the following energy function [12]:

$$E(\hat{m}_{Ref}) = -\sum_{n=1}^{N} \log \sum_{m=1}^{M} e^{-\frac{1}{2}\left|\frac{x_m - y_m}{\sigma}\right|^2} + \frac{\lambda}{2}\Phi(v) \quad (3)$$

where $\Phi(v)$ is a regularization to ensure the displacement field to be smooth. $x_n$ denotes a point of the mesh $m_t$, $y_m$ a point of the transformed mesh $\hat{m}_{Ref}$, respectively. N and M refer to the number of points within the respective mesh. The parameter $\lambda$ determines the trade-off between data fitting and smoothness of the deformation field. We empirically determined a suitable value for this parameter ($\lambda=2.0$).

The reference mesh $m_{Ref}$ is registered to every sample mesh $m_t$. The transformed mesh $\hat{m}_{Ref}$ is labeled $y_t$ for ease of use. The training set is defined as $V=\{m_{Ref}, v_1, \ldots, v_T\}$. We used a Principle Component Analysis (PCA) approach [13] to compute the modes of variation. Applying PCA to the covariance matrix of the centered version of V yields a set of eigenvectors $e_1$ describing the principle modes of variation in the training data set. The eigenvectors are ordered in descending order based on the value of their corresponding eigenvalue. The P largest eigenvectors are stored in the matrix $\Phi=[e_1, \ldots, e_p] \in R^{3N \times P}$. A linear combination of the P principal modes of variation, with $b \in R^P$ as weighting factors, spans a subset of linearized mesh models composed of the given modes of variation:

$$m' = \bar{v} + \Phi b \quad (4)$$

The mean shape $\bar{v}$ is defined as $$\bar{v} = \frac{1}{T+1}\left(m_{Ref} + \sum_{i=1}^{T} v_i\right) \quad (5)$$

For quantitative evaluation of the proposed framework, we used ten clinical data sets with manually annotated pulmonary veins (PV) ostia. These landmarks are labeled RSPV (Right Superior Pulmonary Veins), RIPV (Right Inferior Pulmonary Veins), LSPV (Left Superior Pulmonary Veins), and LIPV (Left Inferior Pulmonary Veins). The quality of the registration is measured based on residual landmark distances and mesh-to-mesh distance. The residual landmark error is defined as the Euclidean distance of the center of corresponding PV ostia and measured after non-rigid CPD registration.

Figure 5A:
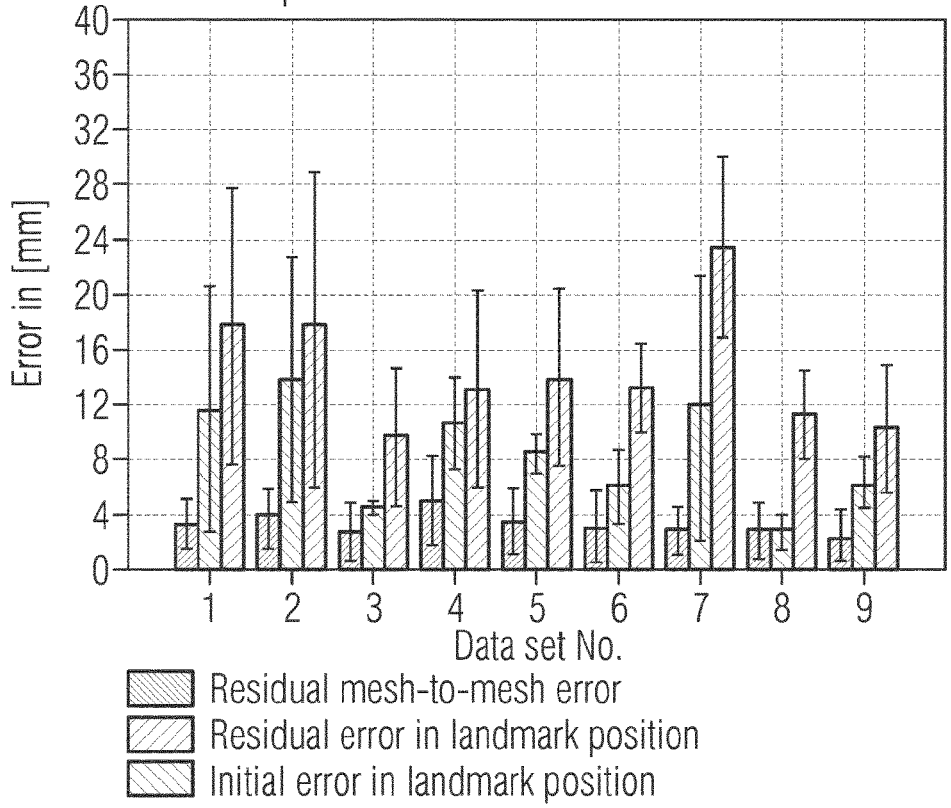
FIG. 5 shows a mean and standard deviation of the residual mesh-to-mesh error, a landmark error after registration and initial landmark error per data set and the mean and standard deviation of the initial and residual landmark error.
Figure 5B:
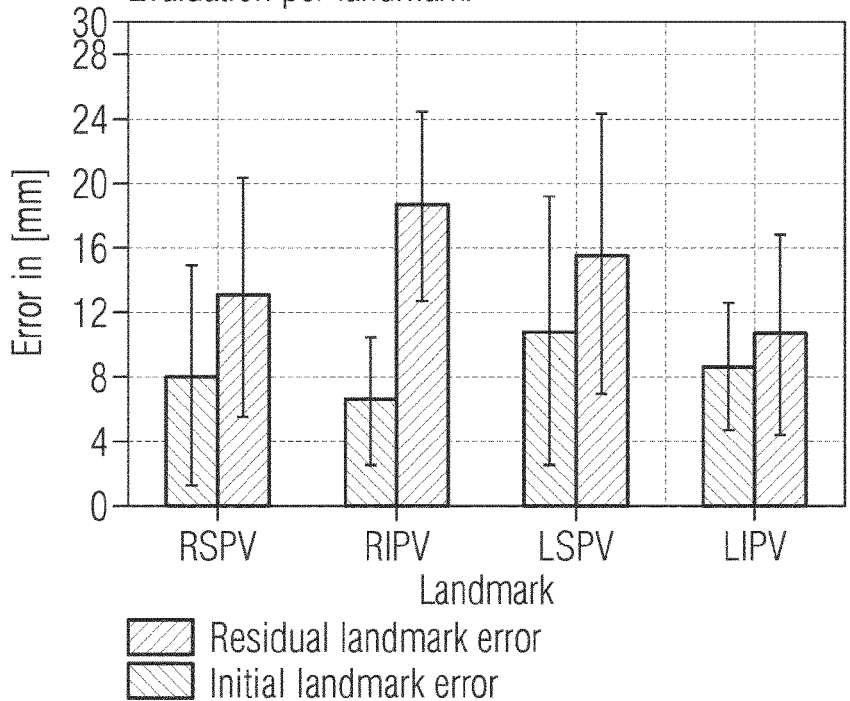

Quantitative registration results are shown in FIG. 5 and discussed in more detail below. FIG. 5(a) shows the average mesh-to-mesh distance, as well as the initial and residual landmark offset per data set. The initial and residual offsets per landmark are shown in FIG. 5(b). The average mesh-to-mesh distance is between 2.5 and 5.1 mm, the average landmark offset is between 2.9 and 13.9 mm. The highest mesh-to-mesh distance occurs at the end of the pulmonary veins. In this case especially on the right inferior PV.

We described a method for left atrium shape modeling using non-rigid point cloud registration. The overall performance of the mesh registration shows a mean mesh-to-mesh error of 3.4 mm over all data sets. The coherent point drift algorithm was capable of dealing with high variations in anatomy. The highest residual mesh-to-mesh distance results from different extents of the pulmonary veins. The average landmark offset was 8.5 mm. Landmarks on the right side of the left atrium, namely RSPV and RIPV, show a lower residual error compared to left sided landmarks LSPV and LIPV. This might be due to the additional pouch on the left side of the left atrium, the left atrial appendage, which is anterior to the PV ostia.

The mesh models of the left atrium also contained a large part of the connected pulmonary veins. Removing or trimming these extensions might improve the accuracy, since these structures show a high variation in shape and size. For the modeling of the atrium, short pulmonary vein ostia would be sufficient. This work is a first step towards our goal of automatic planning of ablation regions for atrial fibrillation procedures. Planning structures could be transferred to augmented fluoroscopy systems used to guide the procedure and overlaid to the X-ray images.

It has been found that the highest mesh-to-mesh distance occurs at the end of the pulmonary veins.

In the following, the comparison of pre-planned ablation lines for the treatment of atrial fibrillation using a common reference model is discussed in more detail.

We used left atrial (LA) surface models of seven different patients to build up a common reference shape. The mesh models are represented as a triangulated mesh structure. The models cover the left atrium as well as a certain extent of the attached pulmonary veins. The length of the pulmonary veins varies from data set to data set For consistency, a pre-processing step has been applied to all LA mesh models. The attached pulmonary veins have been removed from the mesh about 2 cm distal to the LA antrum.

The common reference shape is generated via pairwise non-rigid registration of the LA models. For registration, the mesh is seen as point cloud M consisting of N points $x_i \in R^3$ $$M = m = [x_1^T, \ldots, x_N^T]^T \in R^{3N}. \quad (6)$$

All meshes have the same anatomical orientation, and are zero centered before applying the registration.

We used the Coherent Point Drift (CPD) algorithm [12] to perform the non-rigid point cloud registration. The main benefit of the CPD algorithm is the robustness against nose and outliers while generating smooth deformation fields. A pivot mesh $m_{pivot}$ is registered to template meshes $m_{t_i}$. The variables $t_i$ are used to refer to each of the T=7 template meshes.

Below, we describe how to derive a common reference model. Then we establish mean ablation lines. Afterwards, we evaluate how individual pre-planned ablation lines vary around their mean as we move around the left and right ipsilateral PVs.

In the first step, we selected one left atrium mesh model as pivot element, $$m_{pivot} = m_{t_1} \quad (7)$$

In the next step, we registered the pivot mesh to the remaining template meshes $\{m_{t_2}, \ldots, m_{t_T}\}$. We used the coherent point drift algorithm to compute the non-rigid transformation between the pivot mesh and the other left atrial mesh models. CPD follows a probabilistic approach by considering the alignment of the two point sets as a probability density estimation problem. The basic idea is to fit the Gaussian mixture model (GMM) centroids, represented by the points of the pivot mesh $m_{pivot}$, to the template mesh $m_{t_i}$ by maximizing the likelihood. This optimization is performed with the expectation maximization algorithm. During the optimization the GMM centroids are forced to move coherently as a group, to ensure preservation of the topological structure of the point set.

For each template mesh $m_{t_i}$, the estimated deformation field $\mu_{t_i} \in R^{3N}$ is calculated by registration of the pivot mesh $m_{pivot}$ to $m_{t_i}$. The transformed pivot mesh can then be described as $$\tilde{m}_{t_i} = m_{pivot} + \mu_{t_i} \quad (8)$$

The common reference model or reference data set is defined as the mean shape given by $$m_{ref} = \frac{1}{T-1}\left(\sum_{i=2}^{T} \tilde{m}_{t_i}\right) \quad (9)$$

Putting (8) and (9) together, it is easy to see that the reference mesh is comprised of the selected pivot mesh, and a mean deformation field. In other words, $$m_{ref} = m_{pivot} + \frac{1}{T-1}\left(\sum_{i=2}^{T} u_{t_i}\right). \quad (10)$$

The selection of a proper pivot mesh is important, because it determines the basic shape of the resulting mean mesh. This is why we carefully selected the pivot mesh, making sure that all relevant landmarks, namely the pulmonary veins and left atrium appendage, were clearly expressed.

Planning lines l are represented as a set of points $l=\{x_1, \ldots x_p\}$ with $x \in R^3$. Each template mesh $m_{t_i}$ has two planning lines $l_{t_i,R}$ and $l_{t_i,L}$ attached. They represent desirable ablation lines for right and left sided ipsilateral pulmonary veins, respectively. The planning lines are a subset of the corresponding template mesh, i.e. $\{l_{t_i,R}, l_{t_i,L}\} \subset m_{t_i}$.

To transfer the planning lines from a template mesh onto the reference model, $m_{ref}$ is registered to $m_{t_i}$ using CPD. After registration, the two mesh models are optimally aligned based on the optimization criterion stated in (5). The planning lines $\{l_{t_i,R}, l_{t_i,L}\}$ are now projected onto the transformed reference model $\tilde{m}_{t_i}$ with a nearest neighbor approach. By applying the inverse deformation field, the lines can be mapped onto the reference model $m_{ref}$. There, they are labeled $\hat{l}_{t_i,R}$ and $\hat{l}_{t_i,L}$ for right and left sided planning, respectively.

The mean planning lines are derived from the set of re-mapped ablation lines defined as $$L=\{\hat{l}_{t_i,R}, \hat{l}_{t_i,L}\}_{i=}^{T}. \quad (11)$$

Initially, each planning line consists of an arbitrary number of points. For consistency, each line l was interpolated with a cubic spline, and equidistantly sampled with a fixed number of sample points $P_L$. To investigate the spread and distribution among the pre-planned ablation lines, a common orientation and labeling was enforced. Each planning line represents a closed loop encircling the LA. The point closest to the top is defined as the starting point, and the remaining points are traversed in anterior direction.

After correct alignment of L, mean reference lines $l_{ref,R}$ and $l_{ref,L}$ are generated by averaging corresponding points along the interpolated lines.

In FIG. 1, a schematic view of a left atrium 10 is shown including the pulmonary veins 11, 12, 13, 14. An example of ipsilateral ablation planning lines 15 and 16 is shown.

Figure 3:
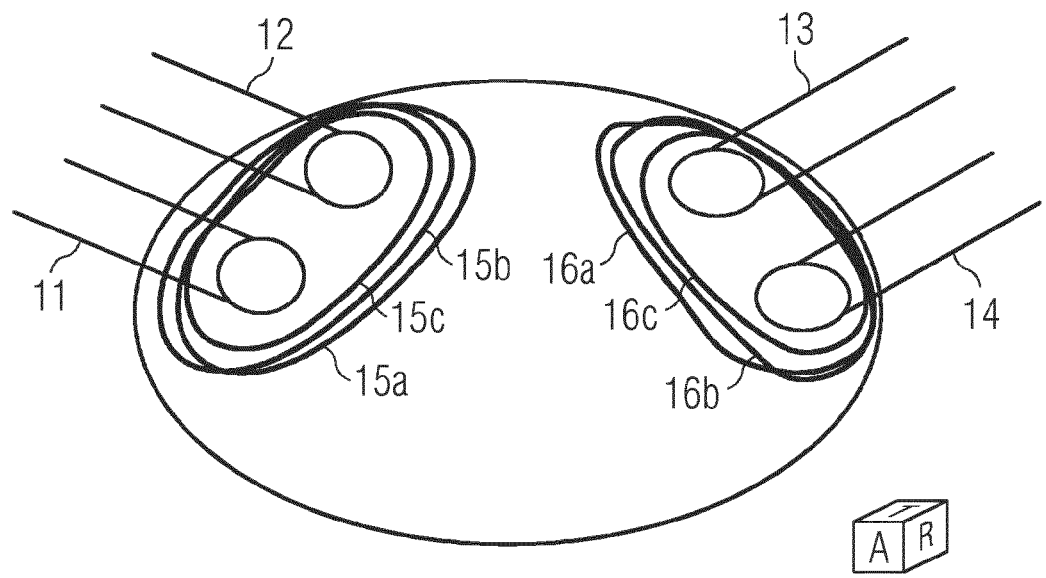
FIG. 3 shows a schematic view of the left atrium with several pre-planned ipsilateral pulmonary vein ablation lines.

In FIG. 3, several pre-planned ablation lines transferred from different meshes are shown. In FIG. 3 three different ablation lines 15a-15c and 16a-16c are shown.

Figure 4:
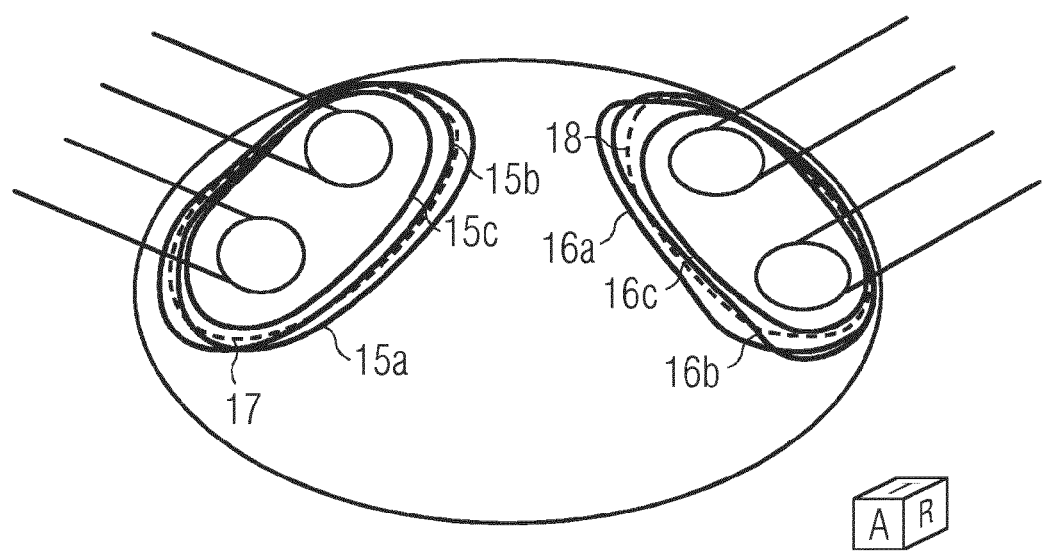
FIG. 4 shows the schematic left atrium of FIG. 3 with pre-planned ablation lines transferred from different data sets and an estimated mean ablation planning line.

In FIG. 4 in addition to the ablation lines already shown in FIG. 3, estimated mean ablation lines 17 and 18 are shown, which were calculated as discussed above.

Figure 6:
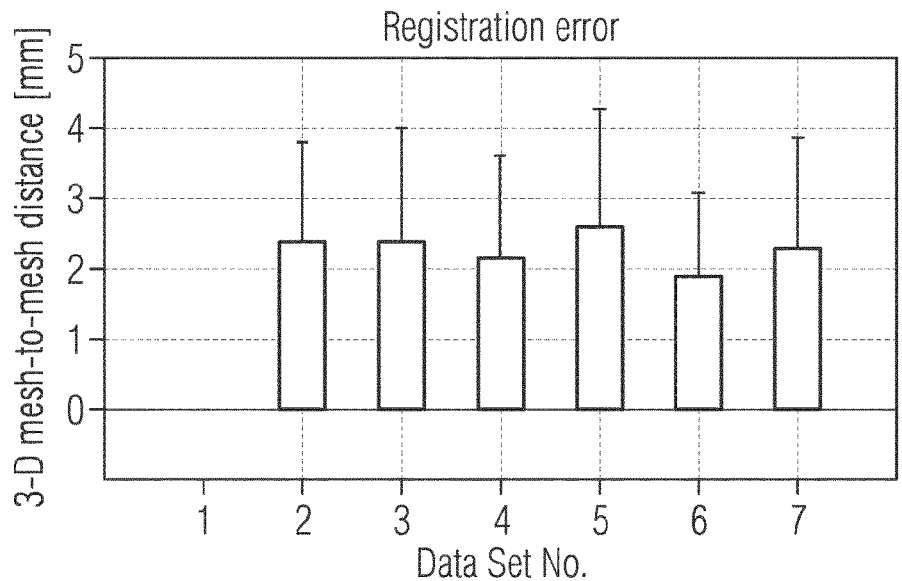
FIG. 6 shows a mean and standard deviation for residual mesh-to-mesh error after non-rigid registration of the reference model to the respective template mesh.

We evaluated our approach on T=7 LA meshes with attached planning lines. The pre-planned ablation lines were placed by an experienced clinician. The registration accuracy of the non-rigid registration of the reference model to the template meshes in terms of residual average mesh-to-mesh error is shown in FIG. 6. The mean residual mesh-to-mesh error calculated over all meshes was 2.0 mm. Data set 1 was selected as pivot mesh for the reference mesh generation. As can be seen in (8), the reference mesh is comprised of the pivot mesh with an additive deformation term. Hence, non-rigid registration of the reference mesh onto data set 1 is possible with a very low residual error, as illustrated in the first column of FIG. 6.

The deviation of the re-mapped planning lines from their respective mean is evaluated as follows. For each point of the reference planning lines $l_{ref,R}$ and $l_{ref,L}$, the distance to the re-mapped planning lines $\hat{l}_{t_i,R}$, $\hat{l}_{t_i,L}$ with i=1 ... T is calculated.

Figure 7:
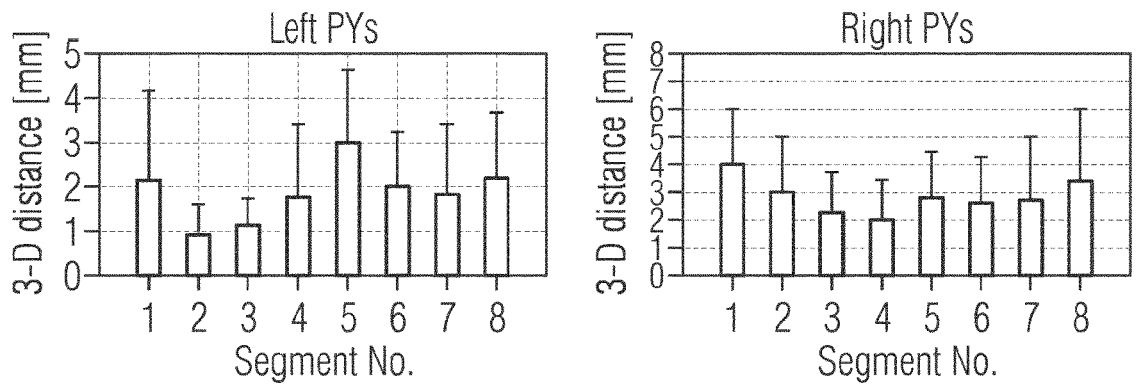
FIG. 7 shows the mean and standard deviation for the distance of pre-planned ablation lines per line segment for left-sided planning lines and right-sided planning lines.
Figure 8:
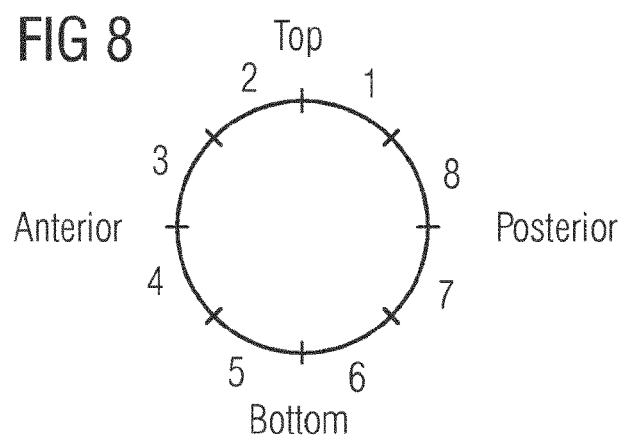
FIG. 8 shows the orientation and labeling of planning line segments.

For further, more anatomically oriented evaluations, the planning lines were divided into eight equally spaced segments, as depicted in FIG. 8, in which a clock schema is used to divide the substantial circular planning lines into different segments. Based on this convention, we present the mean deviation of the individual planning lines per line segment in FIG. 7. Line Segment 1 and 2 are located on the roof of the LA. 5 and 6 are below the inferior PV, and 7 and 8 are on the posterior side of the LA. Note that there is an additional pouch on the left side of the LA, the left atrial appendage (LAA). The LAA is located anterior the left-sided PVs, separated from them by an arrow ridge. The LAA runs on the left side along segments 2 to 5.

The average distance of the re-mapped ablation lines to the reference ablation line was 2.9±1.9 mm and 1.8±1.5 mm for right and left sided planning lines, respectively. The maximum distance of a single planning point to the reference planning line was 8.5 mm and 7.6 mm for right and left side, respectively.

According to our analysis, the average deviation over all individual planning lines that were part of our data set was 2.4±1.8 mm. This results in a region for pre-planned ablation lines that is approximately twice this width. The smallest deviation was encountered in line segments 2 and 3. We believe that this is due to the presence of the ridge between left atrial appendage and left PVs, that leaves limited space for setting up pre-planned ablation lines.

Based on feedback from physicians in this field, our findings appear plausible. In a nutshell, by comparing pre-planned ablation lines placed by an experienced clinician on LA models of actual patients, we found that one seems to have some 5 mm of "wiggle room" despite the presence of prominent anatomical structures. After analyzing the inter-patient variance of manually placed planning lines and learning a general planning pattern, the design of an algorithm for fully automatic pre-planning of ablation lines will be the next step.

In FIG. 9, we summarize the method for evaluating treatment-relevant spatial anatomical information on a reference data set. An example for the treatment-relevant spatial anatomical information are the ablation planning lines in the left atrium.

The method starts in step S90. In a step S91, a reference three-dimensional data set of the atrium is provided. In step S92, further three-dimensional data sets with treatment-relevant spatial anatomical information are provided, e.g. a first data set, a second data set and eventually further data sets. In step S93, the reference data set is registered to each of the data sets provided in step S92.

In step S94, the treatment-relevant spatial anatomical information of each of the data sets provided in step S92 is transferred on the reference data set so that transferred treatment-relevant spatial anatomical information is attached to the reference data set. In step S95, the transferred treatment-relevant spatial anatomical information attached to the reference data set is compared and evaluated. This means that by way of example, a mean and a standard deviation of the planning lines transferred to the reference data set is determined. In the next step S96, a reference treatment-relevant spatial anatomical information is determined, e.g. reference treatment planning lines. The method ends in step S97.

In FIG. 10, a flow chart is shown comprising the steps which can be carried out to compute a reference three-dimensional data set. The method starts in step S100. In another step S101, the different three-dimensional anatomical data sets are provided. In step S102, a pivot data set is selected. This pivot data set may be selected based on visual inspection of the different data sets and serves as basis for the generated reference data set. In step S103, the pivot data set is registered to every of the other three-dimensional data sets. In step S104, it is possible to determine a statistical shape model, e.g. a mean shape as explained in more detail above. In step S105, a reference model or reference data set of the left atrium can be determined as mentioned above in equation 10. As discussed above, the reference model can be comprises of the selected pivot data set and a mean deformation field.

In FIG. 11, a flow chart is shown comprising the steps which can be used to plan an interventional treatment in an atrium. The method starts in step 110. In the method shown in FIG. 11, the transferred treatment-relevant spatial anatomical information is applied to a new data set. In step S111, the reference three-dimensional data set is provided. Furthermore, reference treatment-relevant spatial anatomical information on the reference data set is provided, e.g. as reference treatment planning lines (step S112). In step S113, the new three-dimensional image data set is provided for which the planning lines should be determined. In step S114, the left atrium in the new data set is segmented and in step S115, the reference data set is registered to the new data set. In step S116, the reference treatment-relevant spatial anatomical information is transferred to the new data set to determine planning lines for the new data set. The method ends in step S117.

Figure 2:
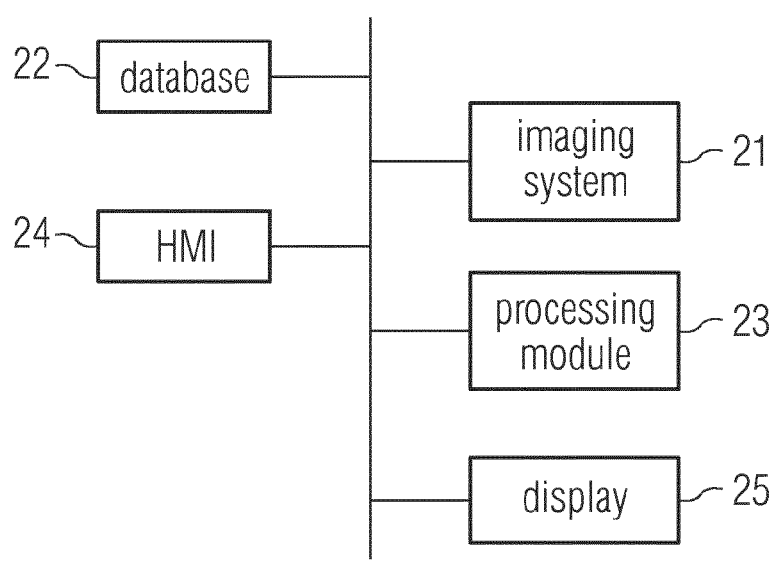
FIG. 2 shows a schematic view of a system that can be used to plan ablation treatment areas.

In FIG. 2, a system is schematically shown with which ablation lines can be evaluated and with which a planning of ablation lines is possible. The three-dimensional images can be generated with an imaging system 21, which can be an MR or CT scanner. The different three-dimensional data sets generated by the imaging system are stored in data base 22. The system may not necessarily contain the imaging system 21. It is also possible that the system only contains the data base 22 with the prestored three-dimensional data sets of the heart or of the atrium. With a processing module 23, the different steps discussed above and the calculations discussed in detail above can be carried out. A human machine interface, HMI, 24 is provided with which a user can interact with the system, e.g. can draw ablation lines, select data sets, etc. The information provided by the system may be displayed on a display 25.

The different components shown in FIG. 2 need not be provided in the form shown in FIG. 2. The functional modules shown in FIG. 2 may be incorporated by another combination of modules. Furthermore, the different modules may be incorporated by hardware or software.

REFERENCES

[1] Heimann T, Meinzer H P, "Statistical shape models for 3D medial image segmentation", *A review. Med Image Anal.* 2009; 13(4): 543-563
[2] Keustermans J, De Buck S, Heidbuechel H, Suetens P, "Automated planning of ablation targets in atrial fibrillation treatment", *Proc SPIE.* 2011; 7962:796207
[3] Stijn De Buck, Frederik Maes, Joris Ector, Jan Bogaert, Steven Dymarkowski, Hein Heidbuechel, and Paul Suetens, "An augmented reality system for patient-specified guidance of cardiac catheter ablation procedures". *IEEE Transactions on Medical Imaging, vol.* 24, no. 11, pp. 1512-1524, November 2005
[4] Martin Koch, Arne Langenkamp, Atilla Kiraly, Alexander Brost, Norbert Strobel, and Joachim Hornegger, "Navigation system with contact force assessment to guide pulmonary vein isolation procedures," in $23^{rd}$ *Conference of the Society for Medical Innovation and Technology (SMIT)*, Tel Aviv, Sep. 13-16, 2011
[5] Felix Bourier, Dejan Vukajlovic, Alexander Brost, Joachim Hornegger, Norbert Strobel and Klaus Kurzidim, "Pulmonary vein isolation supported by MRI-derived 3D-augmented biplane fluoroscopy: A feasibility study and a quantitative analysis of the accuracy of the technique," *Journal of Cardiovascular Electrophysiology,* 2012 [electronic publication ahead of print]
[6] M. Hastenteufel, I. Wolf, C. Christoph, S. Yang, T. Boettger, M. Vetter, and H P Meinzer, "A novel method for planning and visualization of ablation lines for atrial fibrillation treatment," in *Computers in Cardiology.* IEEE, 2004, pp. 13-16
[7] Alexander Brost, Felix Bourier, Andreas Kleinoeder, Jens Raab, Martin Koch, Marc Stamminger, Joachim Hornegger, Norbert Strobel, and Klaus Kurzidim, "AFiT—Atrial Fibrillation Ablation Planning Tool," in *Vision, Modeling and Visualization (VMV),* 2011, pp. 223-230
[8] Roderick Tung, Eric Buch, and Kalyanam Shivkumar, "Catheter ablation of atrial fibrillation," *Circulation,* vol. 126, no. 2, pp. 223-229, 2012
[9] Thomas Arentz, Reinhold Weber, Gerd Brkle, Claudia Herrera, Thomas Blum, Jochem Stockinger, Jan Minners, Franz Josef Neumann, and Dietrich Kalusche, "Small or large isolation areas around the pulmonary veins for the treatment of atrial fibrillation?", *Circulation,* vol. 115, no. 24, pp. 3057-3063, 2007
[10] Kautzner J, Micochova H, Peichl P, "Anatomy of the Left Atrium and Pulmonary Veins—Lessons Learned from Novel Imaging Techniques". *Eur Cardiol.* 2006; 2(1): 89-90
[11] Myronenko A, Song X, "Point set registration: Coherent Point Drift". *IEEE Trans Pattern Anal Mach Intell.* 2010; 32(12):2262-2275
[12] Myronenko A, Song X, Carreira-Perpinan M, "Non-rigid point set registration: Coherent Point Drift". *Adv Neural Inf Process Syst.* 2007; 19:1009-1016

[13] Jolliffe I, "Principal component analysis", *Wiley Online Library;* 2005

The invention claimed is:

1. A method for evaluating treatment-relevant spatial anatomical information among different data sets of different hearts of a plurality of subjects, the method comprising:
   determining, by a system having a database and imaging system, a reference anatomical three-dimensional data set of a left atrium of a heart of a first subject of the plurality of subjects;
   providing, by the system, a first anatomical three-dimensional data set of a left atrium of a heart of a second subject of the plurality of subjects, the first anatomical three-dimensional data set comprising first ablation planning lines;
   providing, by the system, a second anatomical three-dimensional data set of a left atrium of a heart of a third subject of the plurality of subjects, the second anatomical three-dimensional data set comprising second ablation planning lines;
   registering, by the system, the reference anatomical three-dimensional data set to the first anatomical three-dimensional data set and the second anatomical three-dimensional data set;
   transferring, by the system, the first ablation planning lines and the second ablation planning lines to the reference anatomical three-dimensional data set to generate a first transferred ablation planning lines on the reference anatomical three-dimensional data set and a second transferred ablation planning lines on the reference anatomical three-dimensional data set; and
   evaluating, by the system, the first transferred ablation planning lines and the second transferred ablation planning lines, wherein the evaluating comprises determining a mean value, a standard deviation, or a combination thereof of the first transferred ablation planning lines and the second transferred ablation planning lines on the reference anatomical three-dimensional data set for a left atrium of a heart.

2. The method of claim 1, wherein a plurality of additional anatomical three-dimensional data sets of additional hearts of the plurality of subjects are provided with corresponding ablation planning lines,
   wherein the reference anatomical three-dimensional data set is registered to each additional anatomical three-dimensional data set of the plurality of additional anatomical three-dimensional data sets, and the ablation planning lines of each additional anatomical three-dimensional data set of the plurality of additional anatomical three-dimensional data sets is transferred to the reference anatomical three-dimensional data set to determine transferred ablation planning lines on the reference anatomical three-dimensional data set for each additional anatomical three-dimensional data set of the plurality of additional anatomical three-dimensional data sets.

3. The method of claim 2, further comprising:
   dividing the transferred ablation planning lines on the reference anatomical three-dimensional data set into different anatomical sectors; and
   determining a mean deviation of the transferred ablation planning lines for the different anatomical sectors.

4. The method of claim 3, wherein the different anatomical sectors are defined based on a clock schema.

5. The method of claim 1, further comprising:
   determining an average anatomical three-dimensional data set of the left atrium based on the first anatomical three-dimensional data set and the second anatomical three-dimensional data set; and
   determining average ablation planning lines based on the reference anatomical three-dimensional data set taking into account at least the first transferred ablation planning lines and the second transferred ablation planning lines.

6. The method of claim 5, wherein the reference anatomical three-dimensional data set of the left atrium of the heart of the first subject is generated by segmentation of a three-dimensional image data set of the heart of the first subject.

7. The method of claim 1, wherein the reference anatomical three-dimensional data set of the left atrium of the heart of the first subject of the plurality of subjects is generated by segmentation of a three-dimensional image data set of the heart of the first subject of the plurality of subjects.

8. The method of claim 7, wherein the reference anatomical three-dimensional data set, the first anatomical three-dimensional data set, and the second anatomical three-dimensional data set are each provided as a mesh structure, and
   wherein a non rigid mesh registration is used to register the reference anatomical three-dimensional data set to each of the first anatomical three-dimensional data set and the second anatomical three-dimensional data set.

9. The method of claim 8, wherein a coherent point drift method is used for the non rigid mesh registration.

10. The method of claim 9, wherein the mesh structure contains vertices and edges, and
    wherein in the coherent point drift method, Gaussion mixture model centroids, represented by a cloud of vertices of the reference anatomical three-dimensional data set, are fitted to the cloud of vertices of the first anatomical three-dimensional data set and the second anatomical three-dimensional data set.

11. The method of claim 1, further comprising:
    planning an interventional treatment in a left atrium of a heart of an additional subject, wherein a new anatomical three-dimensional data set of the left atrium is provided, wherein the reference anatomical three-dimensional data set of the left atrium of the heart of the first subject is registered to the new anatomical three-dimensional data set to determine ablation planning lines for the new anatomical three-dimensional data set of the left atrium of the heart of the additional subject based on the transferred ablation planning lines of the reference anatomical three-dimensional data set.

12. The method of claim 11, further comprising:
    generating different reference anatomical three-dimensional data sets of the left atrium to take into account different heart anatomies,
    wherein each of the different reference anatomical three-dimensional data sets of the transferred ablation planning lines is evaluated.

13. The method of claim 1, wherein the reference anatomical three-dimensional data set, the first anatomical three-dimensional data set, and the second anatomical three-dimensional data set are each provided as a mesh structure, and
    wherein a non rigid mesh registration is used to register the reference anatomical three-dimensional data set to each of the first anatomical three-dimensional data set and the second anatomical three-dimensional data set.

14. A system configured to evaluate treatment-relevant spatial anatomical information among different data sets of different hearts of a plurality of subjects, the system comprising:

an imaging system;

a database configured to provide, from the imaging system, a reference anatomical three-dimensional data set of a left atrium of a heart of a first subject of the plurality of subjects, a first anatomical three-dimensional data set of a left atrium of a heart of a second subject of the plurality of subjects, and a second anatomical three-dimensional data set of a left atrium of a heart of a third subject of the plurality of subjects, the first anatomical three-dimensional data set comprising first ablation planning lines, the second anatomical three-dimensional data set comprising second ablation planning lines; and a processor, wherein the processor is configured to register the reference anatomical three-dimensional data set to the first anatomical three-dimensional data set and the second anatomical three-dimensional data set, to transfer the first ablation planning lines and the second ablation planning lines to the reference anatomical three-dimensional data set to generate first transferred ablation planning lines on the reference anatomical three-dimensional data set and second transferred ablation planning lines on the reference anatomical three-dimensional data set, and to evaluate the first transferred ablation planning lines and the second transferred ablation planning lines, wherein the evaluation comprises determination of a mean value, a standard deviation, or a combination thereof of the first transferred ablation planning lines and the second transferred ablation planning lines on the reference anatomical three-dimensional data set for a left atrium of a heart.

15. The system of claim 14, wherein the database further comprises a new anatomical three-dimensional data set of a left atrium of a heart of an additional subject, and wherein the system is configured to register the reference anatomical three-dimensional data set of the left atrium to the new anatomical three-dimensional data set of the left atrium to determine ablation planning lines for the new anatomical three-dimensional data set of the left atrium based on the transferred ablation planning lines of the reference three-dimensional data set.

* * * * *